US00PP07908P

United States Patent [19]

Klemm

[11] Patent Number: Plant 7,908

[45] Date of Patent: Jul. 14, 1992

[54] GERANIUM NAMED MARLEVIT

[75] Inventor: Siegfried Klemm, Stuttgart, Fed. Rep. of Germany

[73] Assignee: Klemm & Sohn, Stuttgart, Fed. Rep. of Germany

[21] Appl. No.: 513,930

[22] Filed: Apr. 24, 1990

[51] Int. Cl.[5] ..... A01H 5/00
[52] U.S. Cl. ..... Plt./87.12
[58] Field of Search ..... Plt./68

[56] References Cited

U.S. PATENT DOCUMENTS

P.P. 7,085 12/1989 Hofmann ..... Plt. 68

*Primary Examiner*—Howard J. Locker

[57] ABSTRACT

A new and distinctive Geranium plant particularly distinguished by its deep Tyrian Purple flowers comprising round flower clusters that stand on strong upright stalks above a round full body of dark green leaves which contrast well with the purple flowers. Marlevit grows medium high, but intensive sunshine keeps the plant short.

1 Drawing Sheet

BACKGROUND OF THE PLANT

My new Geranium cultivar originated as a hybrid seedling resulting from an accidental crossing of the variety 'Cherry' (U.S. Plant Pat. No. 7,085) with an unknown pollen parent in 1984 at my nursery in Stuttgart, West Germany. The present seedling of this hybrid bloomed for the first time in 1985 and because of its outstanding color characteristics, it was selected by me for vegetative reproduction which was done by me and under my direction by means of cuttings at Stuttgart. Asexual reproduction of successive generations of this plant by cuttings at Stuttgart for more than four years has shown that its novel and distinguishing characteristics are fixed and hold true from generation to generation.

DESCRIPTION OF THE DRAWING

My new Geranium cultivar is illustrated by the accompanying full color photographic drawing, which shows a potted plant with well developed clusters of relatively large flowers which illustrates their form and their Tyrian Purple coloring, the color rendition being as true to that herein specified as is reasonably possible to obtain by conventional photographic procedures.

DESCRIPTION OF THE PLANT

The following is a detailed description of my new Geranium plant as observed of plants grown both in greenhouse and outdoors at Stuttgart, with the color designation being according to The R.H.S. Colour Chart published by The Royal Horticultural Society of London, England.

THE PLANT

Origin: Hybrid Seedling.
Parentage:
- *Seed parent.*—Cherry, U.S. Plant Pat. No. 7,085.
- *Pollen parent.*—Unknown.

Classification:
- *Botanic.*—*Pelargonium zonal* hybrid.
- *Commercial.*—Zonal Geranium.

Form: Compact middle-high bush.
Height: 22 to 26 cm. from the media surface at the end of September.

Growing rate: Medium.
Growth habit: Upright, compact and vigorous with short internodes.
Branching character: Free branching from the base.
Strength: Medium stands upright without artificial support.
Foliage:
- *Quantity.*—Average with stalked leaf attachment.
- *Shape of leaf.*—Kidney shaped to half round, with bicrenate margin and very light zonation.
- *Size.*—About 7 cm.×4.5 cm.
- *Texture.*—Smooth.
- *Color.*—Upperside — Dark green RHS 137-A. Underside — A lighter green RHS 137-D.

Ribs and veins: Palmate veination.
Petioles:
- *Length.*—About 4 to 6 cm.
- *Color.*—137-B/C.

THE BUD

Size: Medium — About 7 mm. wide and about 14 to 16 mm long.
Shape: Ovoid.
Opening rate: Medium.
Colors of petals:
- *When sepals first divide.*—Violet, 66-B.
- *When petals begin to unfurl.*—50-A.

Sepals:
- *Number.*—5.
- *Shape.*—Ovoid and pointed.
- *Rate of opening.*—Medium.
- *Character.*—When flower opens, sepals stand up.
- *Color.*—Inside light green 143-C. Outside green 143-C.

Calyx:
- *Shape.*—Lozenge.
- *Size.*—Medium.
- *Aspect.*—Smooth.
- *Splitting.*—Calyx does not split.

Flower Stem:
- *Length.*—About 16 cm. and erect.
- *Color.*—Green 137-D.

INFLORESENCE

Blooming habit: Continuous and profusely from early Spring through Fall.
Size of flower: Medium semi-spherical umbel.
Umbel:
*Diameter.*—About 7 to 8 cm.
*Form.*—Semi-spherical, almost round.
*Number of florets per cluster.*—About 50 to 60 during blooming period.
*Length of stem.*—About 16 cm.
Size of floret: Relatively large.
*Diameter.*—About 4.5 to 5 cm.
*Depth.*—About 4 mm.
Borne: Singly a stem of the umbel cluster.
Form: A flattened cup.
Petalage:
*Number.*—8, 1 or 3 petaloids.
*Form.*—Ovoid with entire margins.
*Arrangement.*—Imbricated.
*Persistence.*—5–6 days.
*Texture.*—Soft.
*Appearance.*—Satiny.
*Color.*—Outer petals: 50-A. Inside petals: 57-A. Reverse sides: 52-A.
Disease resistance: Resistant to Botrytis. As observed at Stuttgart, West Germany.
Lasting quality: 15 days on the plant; 6 days as a cut flower.

THE REPRODUCTIVE ORGANS

Stamens:
*Number.*—7.
*Arrangement.*—Around the ovaries.
Anthers:
*Size.*—2 mm.
*Color.*—Red.
Filaments:
*Length.*—About 4 to 6 mm.
*Color.*—Red.
Pollen:
*Color.*—Orange.
Pistils:
*Number.*—One with five individual stigmas.
Styles:
*Length.*—About 5 mm.
*Color.*—Red to pale green.
Stigmas:
*Color.*—Red.
Character of ovaries: About 4 mm. in length and very pubescent.
Fruit:
*Fertility.*—Fertile.
*Shape.*—Ovoid.
*Color at maturity.*—Dark brown.

This Tyrian Purple geranium with dark green leaves starts flowering earlier and more profusely than comparable varieties. The plant blooms from April to late Fall and its height is less in intense sunlight.

The present plant, Marlevit, is somewhat taller than the variety Cherry and has leaves that are darker green in color and have a very light zonation. The flower of Marlevit has a dark red color whereas that of Cherry is more purple. Marlevit has very round umbels that stand on long, upright stems whereas Cherry has umbels of a different shape on somewhat shorter stems. Marlevit has a much better cutting production and the abundance of its florets, which are larger than those of Cherry, provides Marlevit with a more favorable market position than that of Cherry.

I claim:

1. The new and distinctive Geranium plant, substantially as herein shown and described, characterized by its dark green leaves and Tyrian Purple flowers, which bloom continuously and profusely from Spring to late Fall.

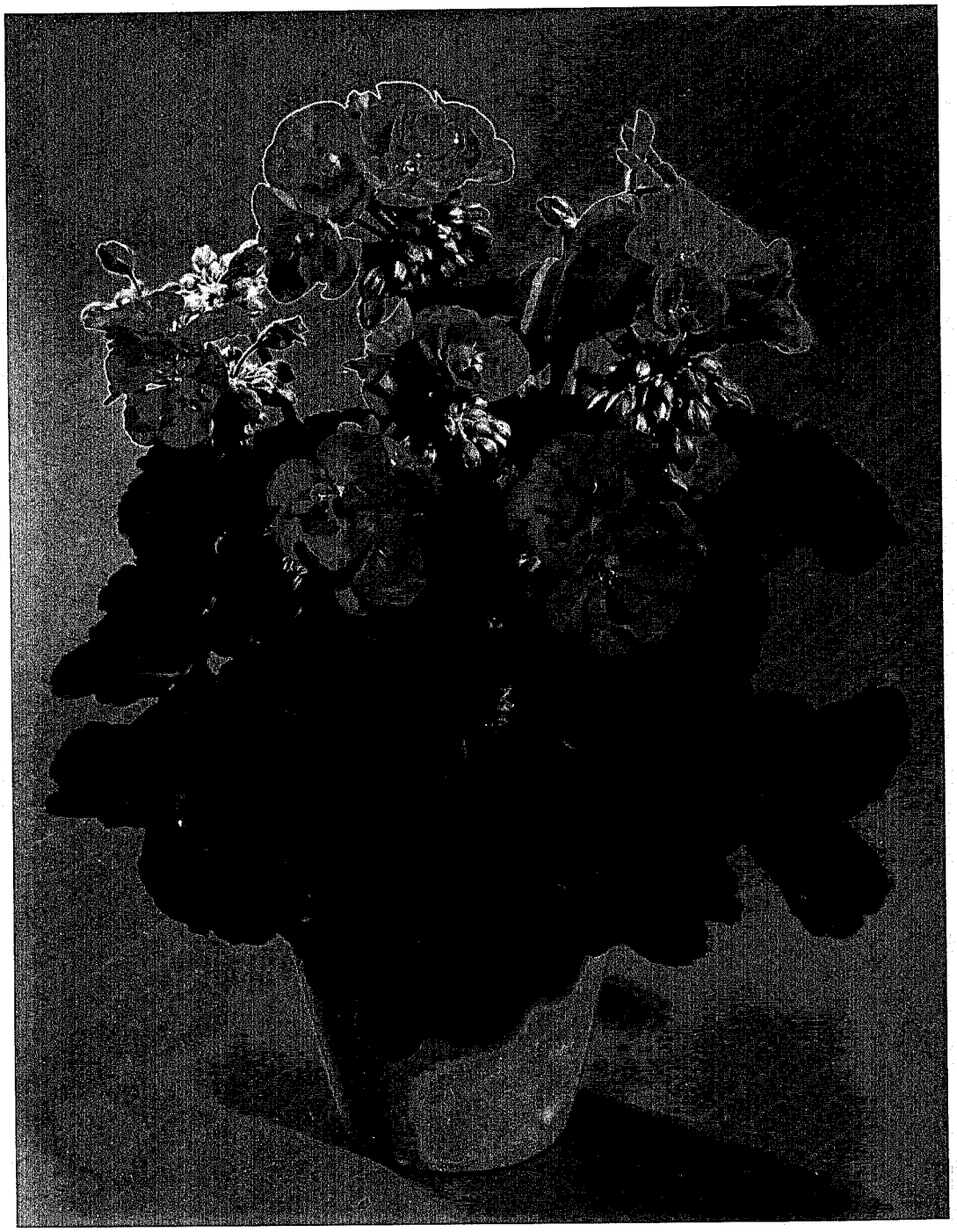

* * * * *